(12) United States Patent
Volker et al.

(10) Patent No.: US 9,970,905 B2
(45) Date of Patent: May 15, 2018

(54) SYSTEM AND METHOD FOR DEFECT MONITORING

(71) Applicant: Nederlandse Organisatie voor toegepast-natuurwetenschappelijk onderzoek TNO, 's-Gravenhage (NL)

(72) Inventors: Arno Willem Frederik Volker, 's-Gravenhage (NL); Petrus Stephanus van Zyl, 's-Gravenhage (NL); Pooria Lotfollah Pahlavan, 's-Gravenhage (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 263 days.

(21) Appl. No.: 14/914,679

(22) PCT Filed: Sep. 1, 2014

(86) PCT No.: PCT/NL2014/050594
§ 371 (c)(1),
(2) Date: Feb. 26, 2016

(87) PCT Pub. No.: WO2015/030592
PCT Pub. Date: Mar. 5, 2015

(65) Prior Publication Data
US 2016/0202213 A1  Jul. 14, 2016

(30) Foreign Application Priority Data

Aug. 30, 2013 (EP) .................................. 13182479

(51) Int. Cl.
*G01N 29/04* (2006.01)
*G01N 29/44* (2006.01)
*G01N 29/07* (2006.01)

(52) U.S. Cl.
CPC ........... *G01N 29/07* (2013.01); *G01N 29/043* (2013.01); *G01N 29/44* (2013.01);
(Continued)

(58) Field of Classification Search
CPC .. G01N 29/043; G01N 29/4472; G01N 29/44; G01N 29/07; G01N 2291/0289; G01N 2291/106; G01N 2291/103
(Continued)

(56) References Cited

U.S. PATENT DOCUMENTS 4,255,798 A  3/1981 Havira
5,351,543 A  10/1994 Migliori et al.
(Continued)

FOREIGN PATENT DOCUMENTS

CN  1560619 A  1/2005
DE  2131786 A1  6/1977
(Continued)

*Primary Examiner* — J M Saint Surin
(74) *Attorney, Agent, or Firm* — Hoffmann & Baron, LLP

(57) ABSTRACT

A defect monitoring system has ultrasound transmitters and receivers on a wall of a structure under test such as a pipeline. The receivers are arranged in an array of locations that substantially encloses an area under test on a wall of a structure under test. The array may comprise two circumferential rings along a pipeline at different axial positions. The array of ultrasound receivers is used to measure signals that result ultrasound that leave the area through the wall for other parts of the wall. From the measured signals backward propagated signals are computed for a location within the enclosed area, compensated for a modelled effect of propagation from the location within the area to the locations of the receivers at the perimeter. The backward propagated signals for the location in the enclosed area are summed over the locations of the receivers to obtain an approximate integral over the perimeter of the area. The integral is used as a normalization factor for the backward propagated (Continued)

signals for the location within the area. In this way reflection and/or transmission coefficients are obtained that are indicative of the size of defects in the wall, independent of calibration of ultrasound coupling coefficients.

19 Claims, 5 Drawing Sheets

(52) U.S. Cl.
CPC . *G01N 29/4472* (2013.01); *G01N 2291/0289* (2013.01); *G01N 2291/103* (2013.01); *G01N 2291/106* (2013.01)

(58) Field of Classification Search
USPC .......................................................... 73/598
See application file for complete search history.

(56) References Cited

U.S. PATENT DOCUMENTS

| | | | |
|---|---|---|---|
| 5,528,557 A | 6/1996 | Horn | |
| 5,804,730 A | 9/1998 | Pfannenstiel et al. | |
| 7,997,139 B2* | 8/2011 | Owens | G01N 29/2412 |
| | | | 702/39 |
| 8,997,550 B2* | 4/2015 | Smith | G01N 29/07 |
| | | | 73/1.82 |
| 9,027,404 B2* | 5/2015 | Singh | G01N 29/043 |
| | | | 73/602 |
| 2002/0105324 A1 | 8/2002 | Kwun et al. | |
| 2004/0095137 A1 | 5/2004 | Kwun et al. | |
| 2004/0216512 A1 | 11/2004 | Kwun et al. | |
| 2005/0075800 A1* | 4/2005 | Batzinger | G01B 7/281 |
| | | | 702/35 |
| 2007/0044560 A1 | 3/2007 | Instanes et al. | |
| 2008/0315872 A1 | 12/2008 | Kwun et al. | |
| 2009/0139337 A1 | 6/2009 | Owens et al. | |
| 2009/0150094 A1 | 6/2009 | Van Velsor et al. | |
| 2009/0271443 A1* | 10/2009 | Haas | G06F 17/30306 |
| 2011/0232385 A1 | 9/2011 | Nanaumi | |
| 2012/0166135 A1 | 6/2012 | Ing et al. | |
| 2013/0100774 A1 | 4/2013 | Brown et al. | |

FOREIGN PATENT DOCUMENTS

| | | |
|---|---|---|
| FR | 2564202 A1 | 11/1985 |
| FR | 2714472 A1 | 6/1995 |
| JP | 02167465 A | 6/1990 |
| JP | 2009092471 A | 4/2009 |
| KR | 20090015596 A | 2/2009 |
| KR | 20100090912 A | 8/2010 |
| WO | 0008459 A1 | 2/2000 |
| WO | 2008103036 A1 | 8/2008 |

* cited by examiner

SYSTEM AND METHOD FOR DEFECT MONITORING

This application is the U.S. National Phase of, and Applicants claim priority from, International Patent Application Number PCT/NL2014/050594 filed Sep. 1, 2014, which claims priority from EP 13182479.9 filed Aug. 30, 2013, each of which is incorporated herein by reference.

FIELD OF THE INVENTION

The invention relates to a system and method for monitoring a structure such as a pipeline for defects.

BACKGROUND

It is known to monitor a structure by detecting reflection of ultrasound waves from within the structure. This makes it possible to detect defects such as cracks in the structure, because defects give rise to ultrasound wave reflection. In particular, defects in a wall of the structure may be detected. As used herein, a wall is a part of the structure that extends from a surface of the structure to a limited distance below the surface, so that it supports ultrasound waves that propagate in a lateral direction, that is a direction parallel to the surface. A wall need not enclose a space within the structure. An ultrasound transmitter (transducer) on the surface of the wall may be used to excite a wave that propagates in a lateral direction. This will be referred to as lateral transmission. An ultrasound receiver on the surface may be used to detect a wave signal due to a wave that propagates in a lateral direction through the wall underneath the receiver. Such a laterally propagating wave will be said to "emerge laterally" or "enter laterally" out of or into an area of the surface adjacent the receiver, without implication that the wave emerges or enters transversely, i.e. in a direction transverse to the surface. An ultrasound transceiver is both an ultrasound transmitter and an ultrasound receiver.

When the structure is a pipeline, a detection arrangement may comprise rings of ultrasound transducers and receivers around the circumference of a pipe, with an axial section of the pipe between the transducers and the receivers. In this case the delay between transmission from the transducers and reception of a reflection at the receivers in the ring provides information about the distance between the ring and a defect in the pipe and the circumferential position of the defect.

Similarly for any structure other than a pipeline, ultrasound transmission between transmitters and receivers at different positions on the wall of the structure may be used. In this case monitoring may be performed by comparing measured transmission with a baseline signal obtained from the structure without defects for each of a number of combinations of transmitters and receivers. Relative calibration of the monitoring signal and the baseline signal may be needed before the comparison to account for things like changes of transfer coefficients between ultrasound in the transducers and ultrasound in the structure.

Beyond mere detection of defects, ultrasound can be used for more detailed analysis of defects. The angle dependence of reflection may be informative about defect geometry. The magnitude of ultrasound reflections grows with defect size. For monitoring purposes it may be important to estimate the size of the defect. Intervention to repair or replace the structure may only be needed once defects exceed a threshold size. In some cases a monitoring system may be installed only after a defect has been found, in order to detect when it develops to a size that requires intervention. Therefore it is desirable for monitoring to determine the magnitude.

However, use of reflection magnitude measurements requires calibration. Apart from defect size, reflection magnitude also depends on other factors, such as transfer coefficients between ultrasound in the transducers and ultrasound in the structure, which may depend on the way in which the transducers are attached and other factors like temperature.

U.S. Pat. No. 4,255,798 discloses inspection of bore holes by means of ultrasound. In particular the quality of the bond of cement around a pipe in the bore hole is determined. A normalized energy bond signal is obtained by taking a quotient of the amplitude of reflections due to reverberation between the inner and outer casing and the amplitude of a casing reflection. In one embodiment the reverberation segment of the reflections is integrated over a particular time span to determine the energy therein. A normalized bond value, representative of the quality of the cement bond is obtained by dividing the integrated reverberation integral by the integrated casing signal.

SUMMARY

Among others it is an object to provide for calibrated structure monitoring.

A defect monitoring system is provided that comprises an array of ultrasound receivers, e.g. an array comprising a first and second ring of transducers around a pipe, or a linear array of receivers, for measuring signals that result from ultrasound that laterally emerges from an area on a wall of a structure under test, i.e. ultrasound that leave the part of the wall in that area through the wall to parts of the wall outside that area, after transmission through the area and/or reflection in the area, in response to ultrasound transmitted by the ultrasound transmitter. The defect monitoring system comprises a signal processing system coupled to the ultrasound receivers, configured to compute respective estimated signals for a location under test in the area on the wall from the measured signals from the ultrasound receivers on an edge of the area (i.e. along part or all of its perimeter). This involves using a model of ultrasound propagation through the wall to account for the effect of propagation from the location such as delay and wave divergence between the location under test and the receivers. The estimation accounts for a modeled effect of ultrasound propagation from the location to the receivers, by undoing that effect and is therefore called back propagation.

The signal processing system determines a normalization factor for the estimated (backward propagated) signals for the location under test from a reference signal computed for that location.

The reference signal may be a sum of the backward propagated signals for that location under test, obtained using measured signals from receivers on opposite sides of the area. Reflection and/or transmission involve measured signals from receivers on different sides of the area. By using a reference signal obtained by summing estimated signals based on measured signals from both sides, a normalized reflection and/or transmission coefficient associated with the location under test may be obtained that preserves the defect dependent amplitude but is independent of properties of the defect monitoring system itself. Alternatively, the normalization factor may be used to inversely normalize a threshold for generating an alert, and/or a model based prediction as part of a comparison with the non-normalized measured reflection and/or transmission coefficient. Signals due to ultrasound that laterally emerges from the area may be distinguished from signals due to ultrasound that laterally enters the area may be selected using time windows based on different time delays between pulse transmission and generation of these signals.

In alternative embodiment the reference signal may be determined by measuring incoming ultrasound that enters the area at the array of receivers (incoming and emerging ultrasound can be distinguished by taking signals from different time windows). From the measurement signals of incoming ultrasound at the receivers an estimated incoming signal at the location under test can be estimated. The estimation accounts for a modeled effect of ultrasound propagation from the receivers to the location under test, and is therefore called forward propagation. In this embodiment using incoming signals the array of receivers need contain only receivers between the transmitter and the area, whereas the embodiment that uses a sum of emerging signal requires receivers both in front of and behind the area, as seen from the transmitter. In the embodiment using incoming signals the receivers are preferably distinct from the transmitter, whereas transducers may be used as the receivers and transmitters in the embodiment that used a sum of emerging signals as a reference. Both alternative may be combined for the computation of the reference signal. For example, the normalization factor may be determined from an average of reference signals obtained by the alternatives.

The defect monitoring system according to any of the preceding claims may comprise an ultrasound transmitter on said wall outside said area and/or, when the reference signal is determined from the second measured signal, on the edge of said area. In the latter case, one of more transceivers may be used, that act both as a receiver in the array and the transmitter.

Preferably, signals corresponding to the same ultrasound propagation mode are measured (at least a same single mode travelling to the defect; for measurements of reflection from or transmission by the defect, the same mode may be selected, or a different mode). If needed, received signals corresponding to a selected mode can be distinguished based on their time of arrival at the receivers.

Preferably, the laterally emerging signals on different sides of the area and/or the laterally incoming and emerging signals on one side are measured in response to the same excitation or, if measured in response to excitations at different time points, using time points at a small time distance (e.g. within a few seconds) selected so that changes in ultrasound propagation properties between the time points can be excluded.

The embodiment using incoming signals has the advantage that it can be used when only one side of the area that contains a possible defect is accessible. The estimation accounts for a modeled effect of ultrasound propagation from the location to the receivers, by undoing that effect and is therefore called back propagation.

In an embodiment, the signal processing system is configured to perform an inverse defect parameter determination process, of estimating defect parameters of a model that predicts the normalized backward propagated signals as a function of the defect parameters. This makes it possible to estimate amplitude related parameters of the defect, such as crack depth and/or length, from the ultrasound measurements without extensive additional calibration.

Similar computations of normalization factors may be performed for a plurality of locations on the wall in the area. This provides more input for the inverse defect parameter determination process, and therefore a possibility to estimate more defect parameters and/or estimate the defect parameters more accurately.

The normalized reflection and/or transmission coefficients for different locations could be used to form an image. However, in a preferred embodiment a large number of reflection and/or transmission coefficients are estimated for a location. In an embodiment, excitations by an array of ultrasound transmitters and/or respective different combined excitations of the ultrasound transmitters in said array are used. In this embodiment respective backward propagated signals for the location may be computed for each excitation and the backward propagated signals for the location may be used to determine normalization factors for respective excitations. Furthermore, normalization factors may be computed for different ultrasound modes. Each may be used to provide more input for the inverse defect parameter determination process, and therefore a possibility to estimate more defect parameters and/or estimate the defect parameters more accurately.

The defect monitoring system may be designed to monitor a pipe. The computation of back propagated signals for a pipe is simple. In an embodiment, the array of ultrasound receivers comprises a first and second sub-array of the ultrasound receivers in the first and second sub-array being located in a first and second circumferential ring along the pipe respectively. Thus the monitoring area is formed by the section of the pipe between the rings. As used herein, a circumferential ring along the pipe may be on the outside of the pipe, or on the inside, on the wall of the pipe.

According to one aspect, a computer program product is provided that comprises instructions for a signal processing system that, when executed by the signal processing system will cause the signal processing system to execute the computation of normalization factors. The computer program product may be a computer readable medium like a semi-conductor memory (e.g. a non-volatile memory), a magnetic or optical disk etc, with a program comprising the instructions stored in it.

A defect monitoring system is provided that has ultrasound transmitters and receivers on a wall of a structure under test, such as a pipeline. The receivers are arranged in an array of locations that substantially encloses an area under test on a wall of a structure under test. The array may comprise two circumferential rings along a pipeline at different axial positions. The array of ultrasound receivers is used to measure signals that result ultrasound that leave the area through the wall for other parts of the wall. From the measured signals backward propagated signals are computed for a location within the enclosed area, compensated for a modelled effect of propagation from the location within the area to the locations of the receivers at the perimeter. The backward propagated signals for the location in the enclosed area are summed over the locations of the receivers to obtain an approximate integral over the perimeter of the area. The integral is used as a normalization factor for the backward propagated signals for the location within the area. In this way reflection and/or transmission coefficients are obtained that are indicative of the size of defects in the wall, independent of calibration of ultrasound coupling coefficients.

BRIEF DESCRIPTION OF THE DRAWING

These and other objects and advantageous aspects will become apparent from a description of exemplary embodiments with reference to the following figures.

DETAILED DESCRIPTION OF EXEMPLARY EMBODIMENTS

Figure 1A:
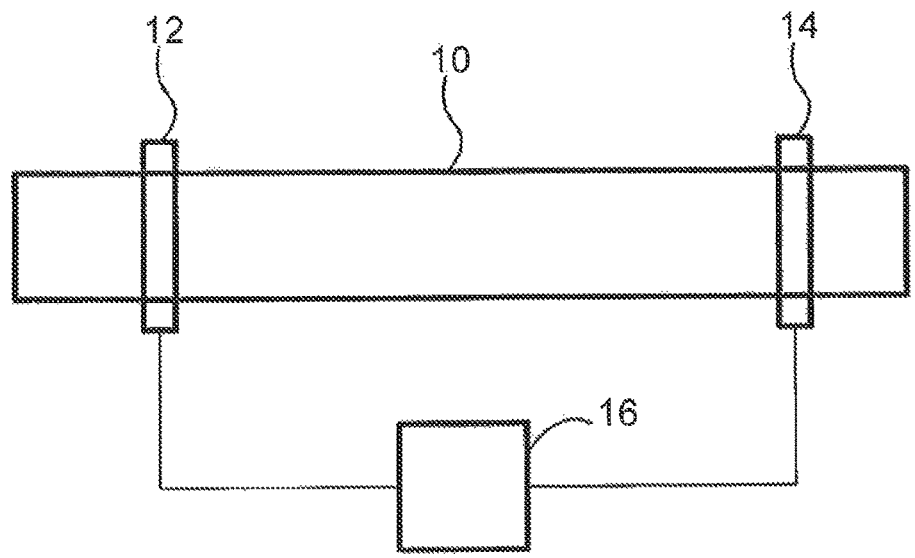
FIG. 1a,b show a system comprising ultrasound transducers on a pipe
Figure 1B:
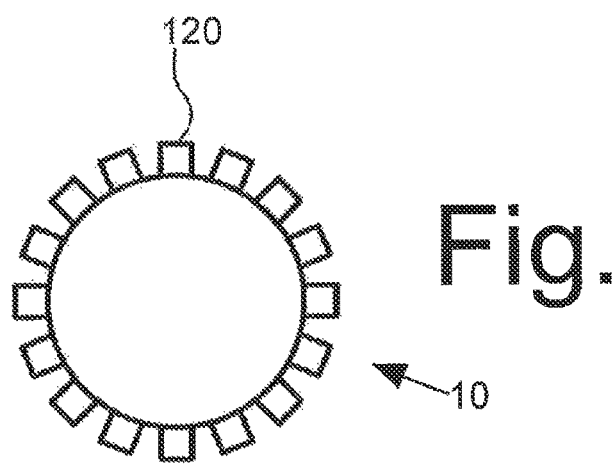

FIG. 1a schematically shows a monitoring system for a pipe 10. The system comprises a first ring 12 of ultrasound transducers, a second ring 14 of ultrasound receivers (which may be ultrasound transducers as well). In an embodiment, pipe 10 has a cross-section that is at least substantially circular, composed of a pipe wall and a hollow interior for transport of fluid. FIG. 1b schematically shows a cross section of pipe 10 at the axial position of first ring 12, with a plurality of ultrasound transducers 120 (only one labelled) in the ring, located at successive circumferential positions on pipe 10. Second ring 14 may have a similar configuration. Furthermore, the monitoring system comprises a processing system 16 coupled to the ultrasound transducers of the first and second ring 12, 14.

A transducer is both an ultrasound transmitter and an ultrasound receiver. The number of transducers 120 in FIG. 1b is shown merely by way of example. For a pipe the number of transducers for a 10 inch (0.25 m) pipe is between thirty and seventy may be used for example. Preferably the transducers are located evenly spaced along the circumference of pipe 10. Preferably the number of transducers is at least so large that the distance between successive transducers along the circumference is less than half the wavelength of the ultrasound waves. This ensures that the wave field along the ring can be reconstructed from ultrasound measurements by the transducers or receivers. However, as is known per se, other ways of positioning along the ring may also ensure this. A slightly larger distance between successive transducers may be used if waves propagating in a direction at small angles to the circumferential direction of pipe may be neglected.

In operation processing system 16 causes transducers 120 of first ring 12 to transmit ultrasound waves and processing system 16 reads out ultrasound measurements obtained by transducers 120 of first ring 12 and by the receivers of second ring 14. From the measurements processing system 16 computes quantitative information about reflection from defects in pipe 10.

The measured ultrasound signal P1 at a transducer 120 in first ring 12 in response to ultrasound excited by that transducer or another transducer in first ring 12 can be modelled by the formula $$P1 = D1 * W2 * R * W1 * S$$

Herein S is a source term that represents ultrasound excitation in pipe 10 by the exciting transducer in first ring 12, R represents a reflection coefficient in pipe 10, D1 is a detection term that represents ultrasound detection by a transducer in first ring 12 and W2, W1 represent the effect of transmission through pipe 10 back and forth between the location of reflection and the receiving transducer in first ring 12 respectively.

When a representation in terms of time and location in pipe 10 is used, D1, W2, R, W1 and S may be space and time dependent functions and the "*" represents spatiotemporal convolution. When a Fourier transformed time dependence is used the temporal convolution becomes a multiplication. In the case of a pipe, a Fourier transformed dependence on circumferential position may be used, in which case the convolution as a function of circumferential position also becomes a multiplication.

By means of transducers 120 of first ring 12 ultrasound measurements $P1(n,i)$ may be obtained for any combination of a transmitting transducer (labelled by i) in first ring 12 and a receiving transducer in first ring 12 (labelled by n). When a Fourier transformed dependence on circumferential position is used, a Fourier transform $P1'(m2, m1)$ of $P1(n, i)$, may be used. $P1'(m2, m1)$ expresses the received frequency component with circumferential frequency m2 of the reflection of ultrasound excited with a circumferentially periodic excitation with circumferential frequency m1.

Similarly the measured ultrasound signal P2 at a transducer in second ring 14 in response to ultrasound excited by that transducer or another transducer in first ring 12 can be modelled by the formula $$P2 = D2 * W3 * T * W1 * S$$

Herein T represents a transmission coefficient at a location in pipe 10, D2 is a detection term that represents ultrasound detection by a receiver in second ring 14 and W3 represents the effect of transmission through pipe 10 from the location of transmission to the receiver in first ring 12.

By means of transducers 120 of first ring 12 and receivers of second ring 14 ultrasound measurements $P1(n,i)$ and $P2(n,i)$ may be obtained or, equivalently, $P1'(m2, m1)$ and $P2'(m2, m1)$ for circumferential frequencies m1, m2.

In the representation in terms of circumferential frequency components the effect of transmission through pipe 10 can be expressed by $$W1(Z,k,\text{omega}) = \exp\{-jZ1 * \text{sqrt}((\text{omega}/c)^2 - k^2)\}$$

Herein Z1 is the axial distance between first ring 12 and the location of reflection, k is the wave vector corresponding to the circumferential frequency of the excitation (its frequency divided by the speed of sound), omega is the temporal frequency of the excitation, c is the speed of sound and j is the square root of minus one. W1 is the ratio of the circumferential frequency components with wave vector k at the axial positions of first ring 12 and the location of reflection. W2 equals W1 in this representation, with the circumferential frequency of the received circumferential frequency component instead of circumferential excitation frequency. For W3 a similar expression holds, but with a Z3 instead of Z1, Z3 corresponding to the distance between the location of reflection and the axial position of second ring 14. The product W3*W1 corresponds to transmission from first and second ring 12, 14. This makes it possible to determine the sum Ztot=Z1+Z3 from measurements of ultrasound transmission between first and second ring 12, 14. Based on such measurements, Ztot−Z1 may be used as Z3 in a computation of W3.

The expression for W1 assumes that wave damping is not significant. If damping is significant the expression may be modified to account for this, for example by adding a damping term with imaginary value to the square root.

Figure 2:
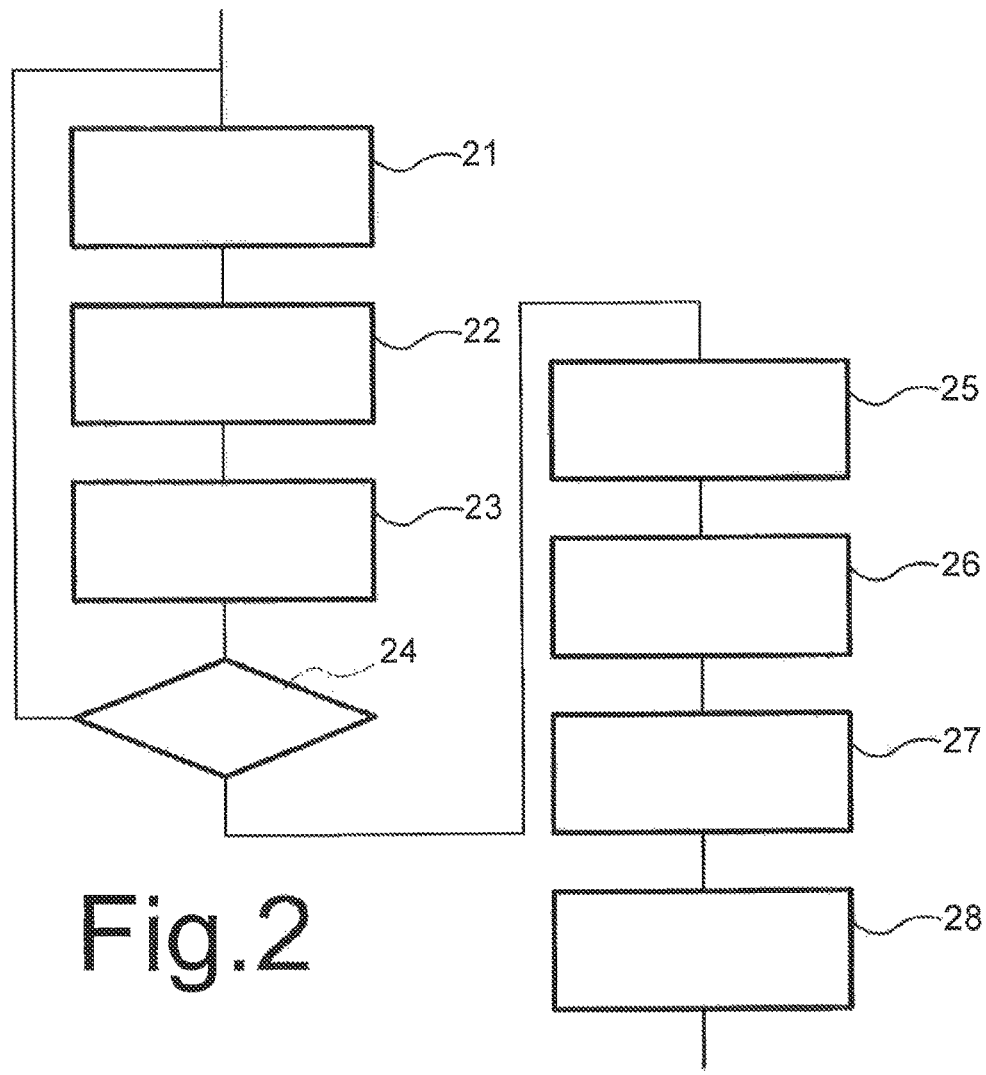
FIG. 2 shows a flow-chart of ultrasound monitoring

FIG. 2 shows a flow chart of operation of operation processing system 16. In a first step 21, processing system 16 causes a transducer 120 (labelled by "i") in first ring 12 to transmit an ultrasound signal. The signal may be a pulse at containing oscillations at a predetermined ultrasound frequency, multiple frequencies or a band of frequencies. In a second step 22, processing system 16 reads received signals P1(j,i) that resulted from the transmission from transducers in first ring 12 (labelled by "j"). In a third step 23, processing system 16 reads received signals P2(m,i), which resulted from the transmission, from receivers in second ring 14 (labelled by "m"). These signals represent signals that travel from the area of the pipe wall between rings 12, 14 to parts of the pipe wall outside that area after transmission through the area or reflection in the area. This will be referred to as lateral emergence. In a fourth step 24 processing system 16 determines whether first to third steps 21-23 should be repeated using a different transducer 120 (with other index "i") in first ring 12 to transmit an ultrasound signal in first step. This is done until all transducer 120 in first ring 12 have been used. Once that has been done, processing system 16 proceeds to a fifth step 25.

Although an embodiment has been described wherein transducers 120 in first ring 12 are used successively in first step, it should be appreciated that alternatively different circumferential frequencies may be used successively, transducers 120 being excited collectively, successively in different relative phase relation corresponding to different circumferential frequencies. In fact any other set of combination of excitation may be used from which a set of excitations at different circumferential frequencies can be synthesized.

Although an embodiment is shown wherein the same first ring 12 of transducers is used both for transmission and reception, it should be appreciated that this is not necessary. For example, a third ring of receivers may be used for reception instead of first ring 12.

In fifth step 25, processing system 16 computes estimated values of the signal at a location z on pipe 10, by computing back propagated signal values P1" to the location z on pipe 10 from each received signal P1 from first ring 12. When the Fourier transformed dependence on circumferential position is used this comprises multiplying P1 by the inverse of W2 for the axial position of the location along pipe 10 for which the back propagated signal value is computed. When a single frequency pulse is used may suffice to compute the back propagated signal values for a single frequency. Alternatively, the received signals may be Fourier analyzed and back propagated signal values may be computed for a plurality of Fourier coefficients for different frequencies.

Generally, backward propagated signals for a location are estimates of signals at that location based on the measured signals at the locations of the ultrasound receivers, according to the assumption that the measured signals result from propagation of ultrasound through the area that includes the location. Generally, ultrasound waves can be represented in a model as a sum of component spatial position "r" dependent wave fields F(m,r), multiplied by freely selectable coefficients c(m) for the respective components (labeled by m). Component wave fields for a frequency equal to a transmission frequency may be used. Optionally, a temporal Fourier transform may be used to resolve different temporal frequency components and the backward propagation may be applied to each temporal frequency.

When the coefficients C(m) are determined from the measured signals according to the assumption that the measured signals result from wave field components that propagate through the area, the backward propagated signals at the location "r" may be determined from a sum of the wave field component values F(m, r) at the location "r" multiplied by the coefficients C(m).

In translationally invariant walls, such as in cylindrical pipes or planes, the different component wave fields F(m,r) at a given temporal frequency correspond to different allowable wave vectors k for that temporal frequency (i.e. m=k). The coefficients C(k) can be computed by a spatial Fourier transform. In the case of component fields F(k, r) that correspond to wave vectors, the value of the component at a location "r" varies according to a phase factor that has a phase that varies according to a scalar product k. r of the wave vector k of the component and the position vector r of the location. If attenuation is significant, a model may used wherein the phase factor is multiplied by an attenuation factor that varies exponentially with distance to the location.

Thus, the determination of the coefficients may comprise computing a Fourier transform. Computing such the sum of the wave field component values F(k, r) at the location multiplied by the coefficients C(k) may comprise computing an inverse Fourier transform of the coefficients C(k) after applying factors to the coefficients that account for location in the wave field component for which the sum is computed.

In a sixth step 26, processing system 16 computes estimated signals a location on pipe 10 by computing back propagated signal values P2" to the location from each received signal P2 from second ring 14. When the Fourier transformed dependence on circumferential position is used this comprises multiplying P2 by the inverse of W3 for the axial position of the location along pipe 10 for which the back propagated signal value is computed.

In the representation with Fourier transformed dependence on circumferential position, a plurality of circumferential frequency components of P1" and P2" for different circumferential frequencies at this axial position is obtained. The inverse Fourier transforms of these circumferential frequency components may be computed to obtain P1" and P2" for an individual circumferential position at this axial position.

In fifth and sixth step 25, 26, processing system 16 performs these computations of P1" and P2" for each of a plurality of locations on pipe 10 between first and second ring 12, 14. In spatial domain representation this results in values P1"(r1, r) and P2"(r2, r), wherein r1 and r2 are circumferential positions of the transducers and receivers on the first and second ring from which the estimated (back propagated) signals are computed, and r is the position between the rings for which it is computed. The computations may be performed for locations on a grid of locations "r" for example. In the representation with Fourier transformed dependence on circumferential position this results in values P1"(k1, r) and P2"(k2, r), wherein k1 and k2 are the circumferential frequencies on the first and second ring. Any sampling distance may be used between the locations "r" for which P1" and P2" are computed. However, below a threshold sampling distance the information in the computed P1" and P2" may become redundant because the information is band limited to a spatial frequency band from zero to maximum spatial frequencies dependent on the ultrasound wavelength used.

In a seventh step 27, processing system 16 computes a reference signal from a sum F of P1" and P2" values for a position "r" summed over positions on the first and second ring, and normalized reflection and/or transmission coefficients in the form of ratios R0=P1"/F and/or T0=P2"/F for each of the plurality of locations r. Thus, normalized coefficients R0(r1, r) and/or T0(r2, r) are computed for reflection/transmission of ultrasound waves from and to positions r1, r2 on the first and second rings to and from the locations r between the rings. Each sum along a ring is used as an approximation for integration of P1" and P2" as a continuous function of position along the ring. Instead of simple sums weighted sums may be used, for example to achieve a better approximation of the integrals, Preferably, the receivers are located evenly distributed along the ring, but if they are not evenly distributed weighted use of weighted sums may improve the approximation.

In the frequency domain the normalized coefficients R0 and/or T0 may be wherein the dependent on one or more of r1, r2 and r has been replaced by a corresponding dependence on a spatial frequency, for example on a frequency of circumferential variation along the circumference of the pipe and/or axial position. Assuming that defects result in elastic scattering, i.e. that the reflection R and transmission T add to one, the ratio R0, T0 computed for a location represents the reflection/transmission for that location independent of calibration. The contribution of W1 and S divides out in the ratios R0, T0 and assuming that D1 and D2 are equal, they D1 and D2 divide out as well. Hence the ratio R0, T0 is independent of calibration. In the representation with Fourier transformed dependence on circumferential position, the sum F can be obtained from the circumferential zero frequency components. Optionally, the sum F for a position r may be computed by first summing the values for individual circumferential frequency components at the axial position of the location r, and subsequently computing the Fourier transform.

The amplitude of the ratio $R0(r1, r)$, or a corresponding R0 wherein the dependence on r1 has been replaced by a corresponding dependence on a spatial frequency, can be used as an estimate of defect (crack) depth at the location r. In an embodiment a predetermined look up table or proportionality constant may be provided based for a source location r1 or spatial source frequency, for converting the amplitude into an estimated crack depth at the location r. In this way a crack depth image representing estimated crack depth as a function of position r can be computed. Processing system 16 may be configured to generate a warning signal when an estimated depth exceeds a threshold. Although embodiments have been described wherein the reflection coefficient is normalized before comparison with the threshold, normalization may also be performed by comparing un-normalized reflection coefficient values with an inversely normalized threshold.

Dependent on the orientation of the crack the reflection for a source location r1 or spatial source frequency may be less than a maximum possible reflection amplitude associated with the crack depth. In an embodiment, a plurality of look up tables or proportionality constants may be provided, each for a respective source location r1 or spatial source frequency. In this way crack depths can be estimated from a plurality of source locations r1 or spatial source frequencies. The results may be combined, for example by taking the maximum crack depth for a location "r" obtained from different source locations r1 or spatial source frequencies. In this way the result may be made less dependent on source location or frequency. Processing system 16 may generate a warning signal when an estimated depth exceeds a threshold. Normalization may be performed by comparing un-normalized reflection coefficient values with an inversely normalized threshold in this case as well, but normalizing the reflection coefficients simplifies the computation. Depth estimation accuracy can be improved beyond this by use of inverse defect model parameter estimation.

In an optional eight step 28, processing system 16 executes an inverse parameter determination process. As is known per se, an inverse parameter determination process makes use of measured data values, a parameterized prediction model for predicting these data values as a function of one of more parameters and a criterion for evaluating differences between the predictions and the measured values. In the inverse parameter determination process a set of values of the one or more parameters is determined that corresponds to a best possible value of the evaluation criterion, or a set of values that approximates such a set of values (best corresponds to minimal difference between measured and predicted data). The inverse parameter determination process may make use of iterative adaptation of the set of parameter values for example.

In the inverse parameter determination process of eight step 28, processing system 16 uses the computed R0 values as measured data and a defect based model as the prediction model. Optionally, T0 may be used instead of or in addition to R0. The defect based model may use a defect line of positions along the defect (e.g. a crack), as well as a defect size (e.g. crack depth) profile as a function of position along the defect line as parameters. The defect line defines a set of positions on the wall of pipe 10. In an embodiment, the defect line may be modelled as a straight line with coordinates of its endpoints on the surface of the pipe as parameters. Alternatively additional parameters may be used to model curves in the defect line. In an embodiment, the defect size (e.g. crack depth) may be modelled as a half ellipse as a function or position along the defect line, with maximum size (crack depth) and optionally eccentricity as parameters of the model. Alternatively, other parameterized functions for crack depth as a function of position along the defect line may be used, with more parameters. Simulated angle dependent ultrasound reflection coefficients can be computed for a defect according to such a model, using a known mechanical model of the pipe. Thus a prediction of the reflection coefficients is defined dependent on the parameters.

In eight step 28, processing system 16 inversely determines the parameters of the model from the computed values of R0 and or T0. Based on the parameters processing system 16 may select whether or not to signal the existence of a defect. For example, if the maximum size (e.g. crack depth) of the defect line and/or a length of the defect line exceeds a predetermined threshold value, processing system 16 may generate a warning signal. A decision whether or not repair is needed may be based on this signal, for example when an estimated crack size exceeds a threshold. Instead of normalization by normalizing the measured reflection coefficients, the normalization may be performed by inversely normalizing the predicted reflection coefficients using the computed sums, and/or by inversely normalizing the threshold.

In an embodiment, the parameters of the defect line and the defect size profile may be estimated in separate steps. For estimating the size profile normalized reflection data R0 may be used. For estimating the parameters of the defect line non-normalized data may suffice.

Although a version of the process has been described wherein transmission of signals from the first ring is used, it should be appreciated that, when the receivers in the second ring are transducers, transmission of signals from the second ring may be used as well. This may yield additional sets of normalized reflections and/or transmission coefficients R0a, T0a. These may be used in addition to the values of R0 and or T0 in the inverse parameter determination process of eight step 28. In this way axially asymmetric defects can be detected.

Figure 3A:
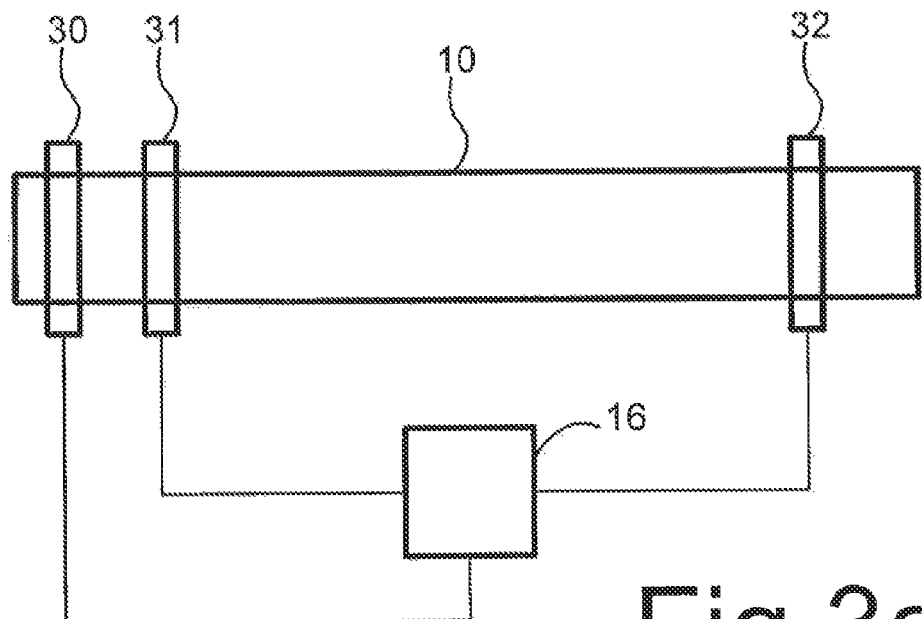
FIG. 3a-c show transducer configurations
Figure 3B:
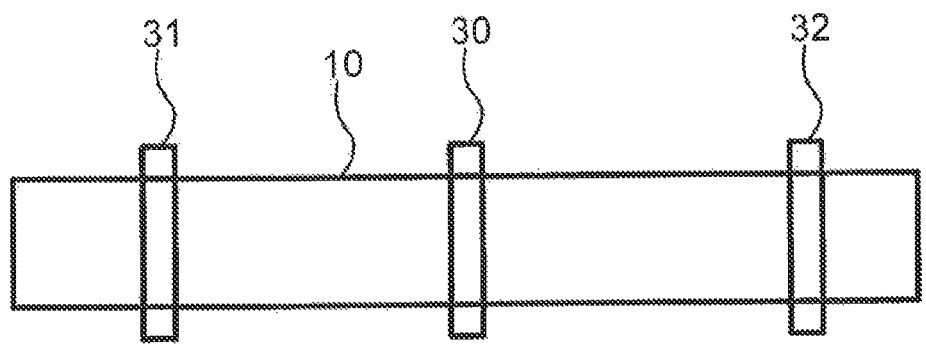

Although an example has been given for a pipe with a ring of transducers and a ring of receivers, it should be appreciated that the method can be applied in other configurations. One feature is first and second ring 12, 14 together receive all ultrasound waves emerging from the pipe section between the rings. This ensures that the sum of the estimated (back propagated) terms add up to the total ultrasound wave factors present at any location in that section from P1 and P2. However, this may be ensured in other ways. FIG. 3a shows a configuration with a ring of transmitters 30 and a first and second ring 31, 32 of receivers. In this case the first and second ring together receive all ultrasound waves from the pipe section between those rings, making it possible to compute a total ultrasound wave factor at each location in that section. However, when a third ring is used it may be necessary to use arrival timing to exclude received signals that arrive from outside the section, leaving only laterally emerging ultrasound signals. FIG. 3b shows a configuration wherein the ring 30 of transmitters is located between the first and second ring 31, 32 of receivers. In this case all received signals are emerging signals. In this case both first and second ring 31, 32 receive both reflected and transmitted signals, which can be distinguished based on timing.

If the combination of rings that are used to receive the signals would be replaced by combination of sets of receivers that leaves an opening for waves from an area to escape undetected, the sum of the estimated (back propagated) terms may not sum up to the total ultrasound wave factor at any location in that area. In this case calculation of a calibration independent ratio R0, T0 may be based on assumptions on extrapolation from the received signals at the available receiver locations to other locations. But this makes the method more heavily dependent on assumptions, thus reducing the reliability of monitoring.

Moreover, it should be noted that in principle the technique for determining R0, R0 is suitable for application to structures other than a circular pipe 10. For example, it may be applied to a pipe of non-circular cross-section and/or a pipe a diameter that varies as a function of axial position. In this case functions W1, W2, W3 different from those disclosed for a constant circular pipe need be used that account for the different cross-sections. Mathematical techniques for deriving such functions are known per se. Alternatively, these functions may be determined by experiment.

As another example, other cylindrical or conical structures may be used (i.e. structures with a wall that has a same shaped cross-section in successive cross-sections perpendicular to an axial direction), with rings of transducers. For example, for a planar strip very similar computations may be used as for a circular pipe, based on ultrasound measurements using rows of ultrasound transducers and receivers on the strip. In this case functions W1, W2, W3 need be used that account for boundary conditions at the edges of the part of the strip between the rows.

In such structures the tractability of the computation is much improved when ultrasound transducers and receivers are uses that are located along respective cross-sections of the structure with virtual flat planes perpendicular to the axial direction and located at different axial positions. However, other arrangements may be used. For example, rings in virtual planes that are oblique to the axial direction may be used.

Figure 3C:
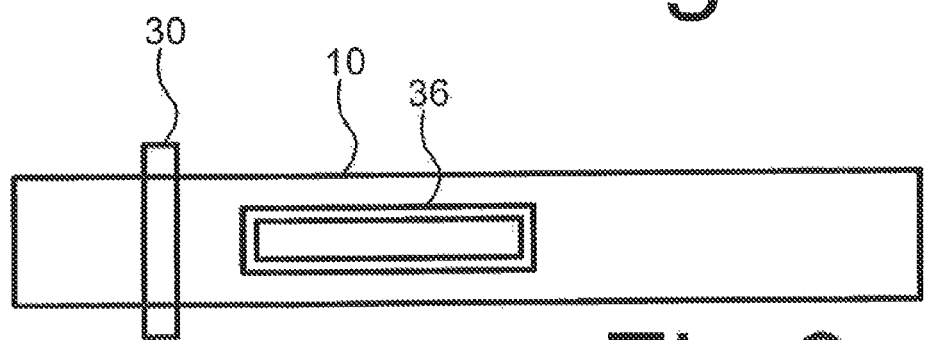

Although the receivers and optionally transducers that act as receivers are preferably located along a first and second closed contour that both encircle the axis of the structure (e.g. the axis of the pipe), in order to monitor the wall area of the structure between these contours, such an arrangement is not indispensible. In some embodiments, it may suffice to use only receivers along a single closed contour, where the contour encircles a region on the structure rather than an axis of the structure. FIG. 3c illustrates such an arrangement with a contour 36 of receivers located next to an array of receivers 20 The contour need not even be a closed contour as long as it encloses a wall area together with one or more edges of the structure. When detections of ultrasound waves that emerge from the wall area within the contour can be identified, the detections of ultrasound waves that exit the wall area can be used to compute the ratio R0 and/or T0 for any point within the wall area. A sum of back propagated signal values from receivers at discrete positions along the contour may be used as an approximation of these signal values as a continuous function of position along the contour. Instead of a simple sum a weighted sum may be used, for example to achieve a better approximation of the integral. Preferably, the receivers are located evenly distributed along the contour, but if they are not evenly distributed weighted use of weighted sums may improve the approximation. Interpolation of signal values to positions between positions of receivers may be used. Similarly, weighting or interpolation may be used to compensate for variations in the orientation of the contour relative to the area under test. For a fixed contour fixed weights or interpolation points may be used.

If separate transmitters are used in addition to the receivers, the transmitters need not be arranged along a closed contour. Measurements can be performed using a single transmitter. In this case reflection and transmission coefficients R0, T0 will become available only for reflection and transmission, by defects, of ultrasound from the location of that transmitter. Under some circumstances this may limit the type of defect for which parameters can be estimated. For example, when the defect is a crack that is aligned with the direction to the location of the single transmitter, detection of the crack may be difficult, and estimation of the length of the crack may be impossible. When transmission from a plurality of positions is used, more reflection and transmission coefficients R0, T0 become available representing reflection and transmission, by defects, of ultrasound from a plurality of locations. This makes it possible to detect and evaluate more defects. Use of a ring of transmitters completely around the pipe facilitates detection of all or most defects.

The walls of a structure like a pipe may support a plurality of different modes of ultrasound propagation, with different propagation speeds. Signals due to different modes can be selected based on travel time and/or transducer-structure coupling. Transmitted and received signals of a single mode suffice for the measurements. In an alternative embodiment a transmitted and/or received signals of a plurality of modes may be distinguished based on travel time and measured individually. This makes it possible to determine reflection and transmission coefficients R0, T0 not only for different combinations of transmitter and receiver locations, but also for different combinations of modes of the incoming and reflected ultrasound signals. This may make it possible to estimate more parameters, such as crack depth, of a defect model and/or to estimate such parameters more accurately.

Figure 4:
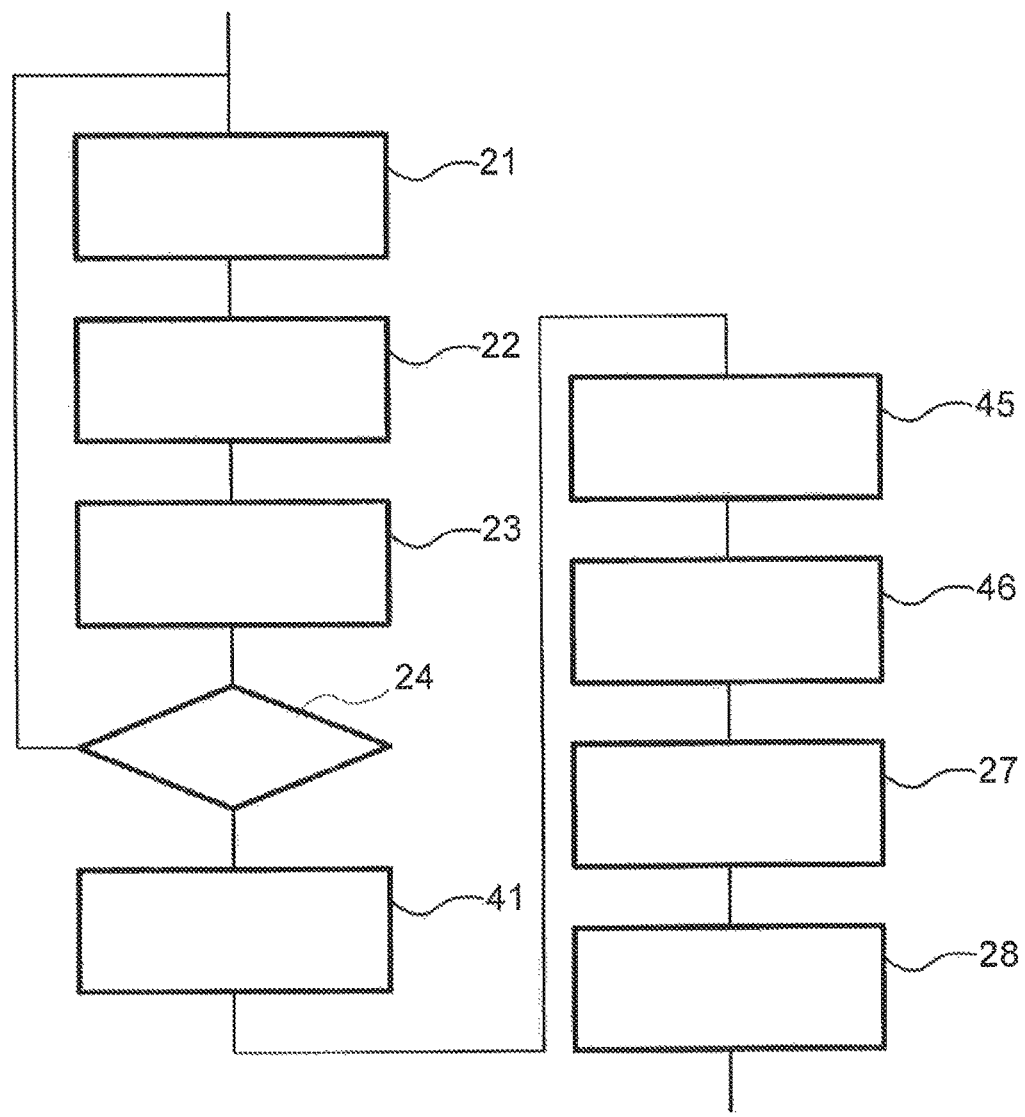
FIG. 4 shows a flow-chart of ultrasound monitoring

In an embodiment, a wall thickness dependent mode is used. Preferably the zero order symmetrical wave mode is used. FIG. 4 shows a flow chart of operation of operation processing system 16 wherein use is made of wall thickness information. Steps that are similar to those of FIG. 2 are labelled by similar numbers. In a first added step 41, after fourth step 24, processing system 16 estimates ultrasound propagation speed (or a thickness corresponding to this speed) as a function of position on the pipe from the signals received at the receivers in second ring 14. A computation for doing so is known from WO2008/103036. An inverse parameter determination process may be used, using a model with parameters that define propagation speed and/or thickness of the wall at a plurality of locations on the pipe. Subsequently, processing system 16 executes modified fifth and sixth steps 45, 46, processing system 16 uses the estimated thickness as a function of position for the back propagation. In this way, defect parameters can be estimated more accurately, using the same measurements also for monitoring thickness. Optionally, eight step 28 may be modified to use a defect model that predicts reflection dependent on the estimated wall thickness at the location of the defect from first added step 41. Processing system 16 may be configured output combined position dependent thickness and defect data as a function of position, for example in the form of a two dimensional image, for monitoring purposes.

According to one aspect a defect monitoring system is provided that comprises an ultrasound transmitter;

an array of ultrasound receivers, for measuring signals that result from ultrasound that emerges laterally from an area on a wall of a structure under test in response to ultrasound transmitted by the ultrasound transmitter;

a signal processing system coupled to the ultrasound receivers, configured to read the measured signals from the ultrasound receivers;

compute respective backward propagated signals for a location in the area on the wall from the measured signals from the ultrasound receivers, using a model of ultrasound propagation through the wall to compute the backward propagated signals;

determining a normalization factor for the backward propagated signals for the location from a sum of the backward propagated signals for that location.

Figure 5:
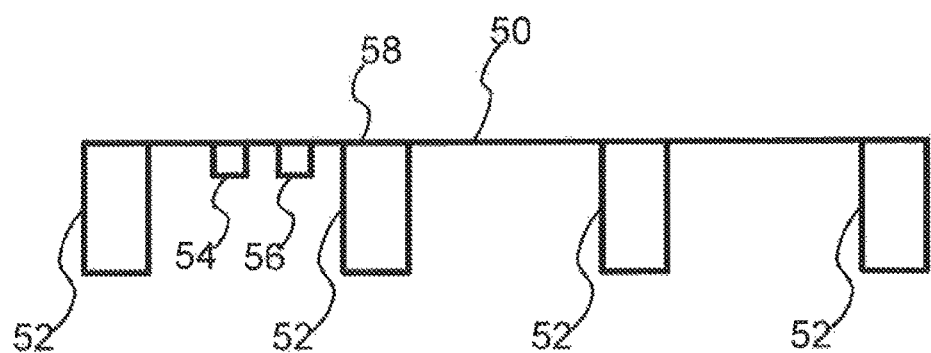
FIG. 5 shows ultrasound transmitters and receivers on a planar structure

FIG. 5 shows an ultrasound transmitter 54 and receiver 56 on a planar structure 50, like a bridge deck, which is has stiffeners 52 attached to it. As used herein, the bridge deck will be called a wall of the bridge structure, although of course the deck need not be an enclosing wall of a space within the bridge. Receiver 56 is part of an array of receivers and transmitter 54 may be part of a plurality of receivers. The transmitters 54 and receivers 56 may be provided in a linear row, along a direction parallel to the row.

In such a configuration of a structure with stiffeners connected to it, it may be difficult to place receivers or transceivers all around an area that may contain a defect. For example, if the location 58 of a defect is enclosed by a U shaped stiffener, the space in the U shape may not be accessible.

In this case an alternative measurement may be used, wherein ultrasound is transmitted from one or more transmitters 54 to the location 58 of a possible defect via locations of an array of ultrasound receivers 56. The receivers 56 in the array measure resulting ultrasound signals. Based on time windows, a processing system (not shown) may extract measurements of signals due to waves traveling outwards from the transmitter or transmitters 54 and measurements of signals due to reflected waves. The measurements of signals due to reflected waves may be normalized using measurements of signals due to outward waves after compensation for propagation to and from the location 58 of the possible defect.

Figure 6:
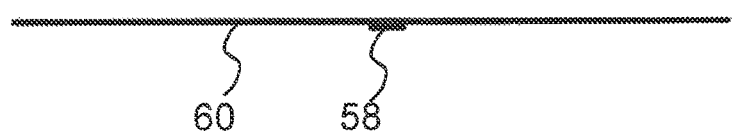
FIG. 6 shows a configuration of ultrasound transmitters and receivers

FIG. 6 schematically shows an example of a configuration of ultrasound transmitters 54 and receivers 56 viewed from a direction perpendicular to the planar structure. A connection line 60 of the planar structure to a stiffener is shown as a line. At least one transmitter is used. By way of example a row of transmitters 54 is shown (only one labeled), the row extending in parallel with connection line 60. An array of receivers 56 is used. By way of example a row of receivers 56 is shown (only one labeled), the row extending in parallel with connection line 60. In an embodiment the array of receivers 56 consists of 128 receivers.

In an embodiment, the processing system uses the measurements of signals due to outward waves to estimate a resulting incoming ultrasound signal at the location 58 of the possible defect. Similarly, the processing system uses the measurements of signals due to reflected waves to estimate a resulting ultrasound reflected (including scattered) signal at the location 58 of the possible defect. The processing system uses the estimated resulting incoming ultrasound signal as a reference signal to determine a normalization factor for the estimated resulting ultrasound reflection. For example, the processing system may compute a ratio of the estimated resulting ultrasound reflection and the estimated resulting incoming ultrasound signal.

The processing system may repeat the computation for different locations 58 based on the same measured signals, or signals obtained using different transmissions. In this way location dependent ratios can be obtained.

This alternative is distinguished from the previous examples in that the normalization is based on measured outward travelling waves that have not yet reached the defect, rather than waves that emerge from an area that contains the defect after a delay sufficient to reach the defect. Also, the alternative does not require receivers for receiving waves that have been transmitted by the defect, although such receivers may be used if that is possible.

When a planar structure 50 is used, a model of propagation may be used that represents the ultrasound in the planar structure as a sum of components that correspond to different wave vectors, amplified by coefficients that depend on how the waves are transmitted and reflected/scattered. If measurements for a given temporal frequency are used, the model may define wave vectors for that frequency.

The processing system may compute the coefficients for the outward and reflected waves from the extracted measurements of the outward and reflected waves. In this case the processing system may compute the ultrasound wave at the location 58 of a possible defect by applying phase factors and optionally attenuation factors to the coefficients, dependent on the wave vectors and the location 58. By way of example, processing system may use a spatial Fourier transform of the measured signals as a function of position along the array of receivers may be used to compute the coefficients. Optionally, a temporal Fourier transform may be used to resolve different temporal frequency components, in order that wave vectors corresponding to different temporal frequencies can be used.

Although this alternative has been described for a structure with stiffeners, it should be appreciated that it can also be used for structures without stiffeners.

Preferably, the receivers 56 in the array of receivers are located so that adjacent receivers are at a distance of no more than half a wavelength of the ultrasound in the structure. Ultrasound from the one or more transmitters 54 reaches the location 58 or locations for which the computations are performed from a range of directions. Narrower ranges of directions can be defined over which substantially all (e.g. all but five percent) of the wave energy from this range of direction reaches the location 58 or locations. Preferably the array of receivers extends over this range of directions, or at least over such a narrower range. Similarly, the array of receivers extends over a further range of directions wherein all or substantially reflected (including scattered) ultrasound energy is reflected. Although the array of receivers has been illustrated by means of a linear array, which simplifies the computations, it should be appreciated that other configurations may be used.

The invention claimed is:

1. A defect monitoring system for monitoring a defect at a location under test within an area on a wall of a structure under test, the system comprising
    an array of ultrasound receivers on said wall at an edge of the area;
    a signal processing system coupled to the ultrasound receivers, configured to
    receive first measured signals from the ultrasound receivers, detected from ultrasound that emerges laterally from the area;
    compute a first estimated signal at the location under test within the area, based on the first measured signals, using a model of ultrasound propagation through the wall to compute the first estimated signal at said location under test from the first measured signals;
    determine a normalization factor for the first estimated signal by computing a reference signal at said location under test according to said model, based at least partly on second measured signals detected by further ultrasound receivers in the array from ultrasound that emerges laterally from the area, and/or third measured signals detected by the ultrasound receivers in the array from ultrasound that enters laterally into the area.

2. A defect monitoring system according to claim 1, wherein the signal processing system is configured to compute the reference signal by
    receiving the second measured signals detected by the further ultrasound receivers from ultrasound that emerges laterally from the area, the area being located between the further ultrasound receivers and the ultrasound receivers used to receive first measured signals,
    computing a second estimated signal at the location under test using said model, based on the second measured signals and
    computing the reference signal from a sum of the first and second estimated signal at the location under test;
    and/or by
    receiving the third measured signals detected by the ultrasound receivers used to receive first measured signals, from ultrasound that laterally enters the area at those ultrasound receivers.

3. A defect monitoring system according to claim 1, wherein the signal processing is configured to compute the reference signal from said sum of the first and second estimated signal, the defect monitoring system comprising an array of ultrasound transmitters, the signal processing system being configured to
    read, from the ultrasound receivers, sets of the first measured signals and the second measured signals that result from lateral emergence of ultrasound from the area in response to ultrasound excitations by respective ultrasound transmitters in said array of ultrasound transmitters and/or respective different combined excitations of the ultrasound transmitters in said array of ultrasound transmitters;
    compute respective first and second estimated signals at the location under test for each excitation from the sets of first and second measured signals from the ultrasound receivers, using said model;
    determine the normalization factor for the first estimated signals at the location under test for each excitation by means of a sum of the first and second estimated signal at the location under test based on the set of first and second measured signals for that excitation.

4. A defect monitoring system according to claim 1, wherein the signal processing system is configured to determine the normalization factor for the first estimated signals for each of a plurality of locations under test on the wall.

5. A defect monitoring system according to claim 1, wherein the signal processing system is configured to perform an inverse defect parameter determination process, comprising estimating values of defect parameters of a model that predicts the normalized first estimated signals as a function of the defect parameters.

6. A defect monitoring system according to claim 1, comprising an ultrasound transducer that acts as the ultrasound transmitter and one of the ultrasound receivers in the array of ultrasound receivers for determining the first measured signal.

7. A defect monitoring system according to claim 1, wherein the signal processing is configured to compute the reference signal from said third measured signal, the defect monitoring system comprising an ultrasound transmitter on said wall, the ultrasound receivers of the array being located between the ultrasound transmitter and said area.

8. A defect monitoring system according to claim 3, comprising an array of ultrasound transducers each configured to act as a respective one of the ultrasound transmitters in the array of ultrasound transmitters and as a respective one of the ultrasound receivers in the array of ultrasound receivers for determining a respective one of the first measured signals.

9. A pipe monitoring system comprising the defect monitoring system of claim 1, and a pipe, the array of ultrasound receivers being located on the pipe, the signal processing system being configured to treat the pipe as said structure.

10. A pipe monitoring system according to claim 9, wherein the area is an axial section of the pipe, the array of ultrasound receivers comprises a first and second sub-array of the ultrasound receivers, the first and second sub-array being located in a first and second circumferential ring along the pipe on opposite sides of the axial section respectively.

11. A surface monitoring system comprising the defect monitoring system of claim 1, said wall and a stiffener connected to said wall as said structure, wherein the area comprises a part of the wall between the array of ultrasound receivers and a connection between the stiffener and the wall.

12. A defect monitoring method, for monitoring a defect at a location under test within an area on a wall of a structure under test, the system comprising
    transmitting ultrasound laterally through the wall into said area
    using an array of ultrasound receivers on said wall at an edge of the area to obtain first measured signals detected from ultrasound that emerges laterally from the area;
    computing a first estimated signal at the location under test within the area, based on the first measured signals, using a model of ultrasound propagation through the wall to compute the first estimated signal at said location under test from the first measured signals;
    computing a reference signal at said location under test according to said model, based at least partly on second measured signals detected by further ultrasound receivers in the array from ultrasound that emerges laterally from the area, and/or third measured signals detected by the ultrasound receivers in the array from ultrasound that enters laterally into the area;

determining a normalization factor for the first estimated signal from the reference signal.

13. A defect monitoring method according to claim 12, comprising computing the reference signal by
receiving the second measured signals from the further ultrasound receivers, the area being located between the further ultrasound receivers and the ultrasound receivers used to receive first measured signals,
computing a second estimated signal at the location under test using said model based on the second measured signals, and
computing the reference signal from a sum of the first and second estimated signal at the location under test; or
by receiving the third measured signals detected by the ultrasound receivers used to receive first measured signals, from ultrasound that laterally enters the area at those ultrasound receivers.

14. A defect monitoring method according to claim 12, comprising
exciting ultrasound excitations with an array of ultrasound transmitters at different locations on the wall, and/or respective different combined excitations of the ultrasound transmitters;
using an array of ultrasound transmitters to measure sets of the first and second measured signals in response to ultrasound excitations by respective ultrasound transmitters in said array of ultrasound transmitters and/or respective different combined excitations of the ultrasound transmitters in said array of ultrasound transmitters;
compute respective first and second estimated signals for the location for each excitation from the each set of first and second measured signals from the ultrasound receivers for the excitation, using said model of propagation through the wall;
determining the normalization factor for first and second estimated signals for the location for each excitation by means of a sum of the first and second estimated signals for the location of that excitation.

15. A defect monitoring method according to claim 12, comprising determining the normalization factor for the backward propagated signals for each of a plurality of locations on the wall.

16. A defect monitoring method according to claim 12, comprising using an inverse defect parameter determination process to estimate defect parameters of a model that predicts the normalized backward propagated signals as a function of the defect parameters.

17. A pipe monitoring method including the steps of claim 12 using a pipe as said structure with sub-arrays of said array of ultrasound receivers located in a first and second circumferential ring along the pipe on opposite sides of a axial section of the pipe respectively.

18. A surface monitoring method including the steps of claim 12 using a surface connected to a stiffener as said structure, wherein the area comprises a part of the wall between the array of ultrasound receivers and a connection between the stiffener and the wall.

19. A computer program product comprising instructions for a signal processing system that, when executed by the signal processing system will cause the signal processing system to execute the method of claim 12.

* * * * *

UNITED STATES PATENT AND TRADEMARK OFFICE
CERTIFICATE OF CORRECTION

PATENT NO. : 9,970,905 B2
APPLICATION NO. : 14/914679
DATED : May 15, 2018
INVENTOR(S) : Arno Willem Frederik Volker, Petrus Stephanus Van Zyl and Lotfollah Pahlavan It is certified that error appears in the above-identified patent and that said Letters Patent is hereby corrected as shown below:

On the Title Page

Item (72) - Please amend the inventor's name
Now reads: "Pooria Lotfollah Pahlavan"
Should read: --Lotfollah Pahlavan--

Signed and Sealed this
Thirty-first Day of July, 2018

Andrei Iancu
*Director of the United States Patent and Trademark Office*